US00PP33027P2

(12) United States Plant Patent
Ammerlaan

(10) Patent No.: US PP33,027 P2
(45) Date of Patent: May 4, 2021

(54) ***ECHEVERIA* PLANT NAMED 'OVPEARLS08'**

(50) Latin Name: *Echeveria pulidonis*
Varietal Denomination: OVPEARLS08

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 16/899,872

(22) Filed: Jun. 12, 2020

(30) Foreign Application Priority Data

Nov. 27, 2019 (QZ) ..... PBR 2019/3116

(51) Int. Cl.
*A01H 5/12* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373
CPC ..... A01H 6/32
See application file for complete search history.

*Primary Examiner* — Anne Marie Grunberg
(74) *Attorney, Agent, or Firm* — Samuel R. McCoy, Jr.

(57) ABSTRACT

A new and distinct variety of *Echeveria* plant named 'OVPEARLSO8' which is characterized by a flattened profile with relatively narrow foliage that is somewhat loosely held in a basal rosette, green and moderately glossy foliage which is narrowly margined dark greyed-purple and becoming more broadly margined at the apex, light suffusion of greyed-purple across most of the abaxial foliar surface, and involute foliar margins at and near the apex. The new variety has shown to be uniform and stable in the resulting generations from asexual propagation.

4 Drawing Sheets

CROSS REFERENCE TO RELATED APPLICATIONS

This application claims priority to the Community Plant Variety Rights application number 2019/3116, filed on Nov. 27, 2019, which is herein incorporated by reference.

Latin name of the genus and species: The Latin name of the genus and species of the novel variety disclosed herein is *Echeveria pulidonis*.

Variety denomination: The inventive variety of *Echeveria* disclosed herein has been given the variety denomination 'OVPEARLSO8'.

BACKGROUND OF THE INVENTION

Parentage: 'OVPEARLSO8' is a naturally-occurring, whole-plant mutation of an unnamed *Echeveria pulidonis* plant (not patented) which was discovered by the inventor in March of 2009 at a commercial greenhouse in Bleiswijk, the Netherlands. The mutation was noted for its blue-gray foliage with conspicuous dark red margins and leaves that are strongly curled upward and inward at the distal margins.

Asexual Reproduction: Asexual reproduction of the new cultivar 'OVPEARLSO8', by way of rooting leaf cuttings, was first initiated in March of 2009 at the inventor's commercial greenhouse in Bleiswijk, the Netherlands. Through eight subsequent generations, the unique features of this cultivar have proven to be stable and true to type.

SUMMARY OF THE INVENTION

The cultivar 'OVPEARLSO8' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVPEARLSO8'. These characteristics in combination distinguish 'OVPEARLSO8' as a new and distinct *Echeveria* cultivar:

1. 'OVPEARLSO8' exhibits a flattened profile with relatively narrow foliage that is somewhat loosely held in a basal rosette; and
2. 'OVPEARLSO8' exhibits green, moderately glossy foliage which is narrowly margined dark greyed-purple, becoming more broadly margined at the apex; and
3. 'OVPEARLSO8' exhibits light suffusion of greyed-purple across most of the abaxial foliar surface.
4. 'OVPEARLSO8' exhibits involute foliar margins at and near the apex.

BOTANICAL DESCRIPTION OF THE PLANT

Figure 1:
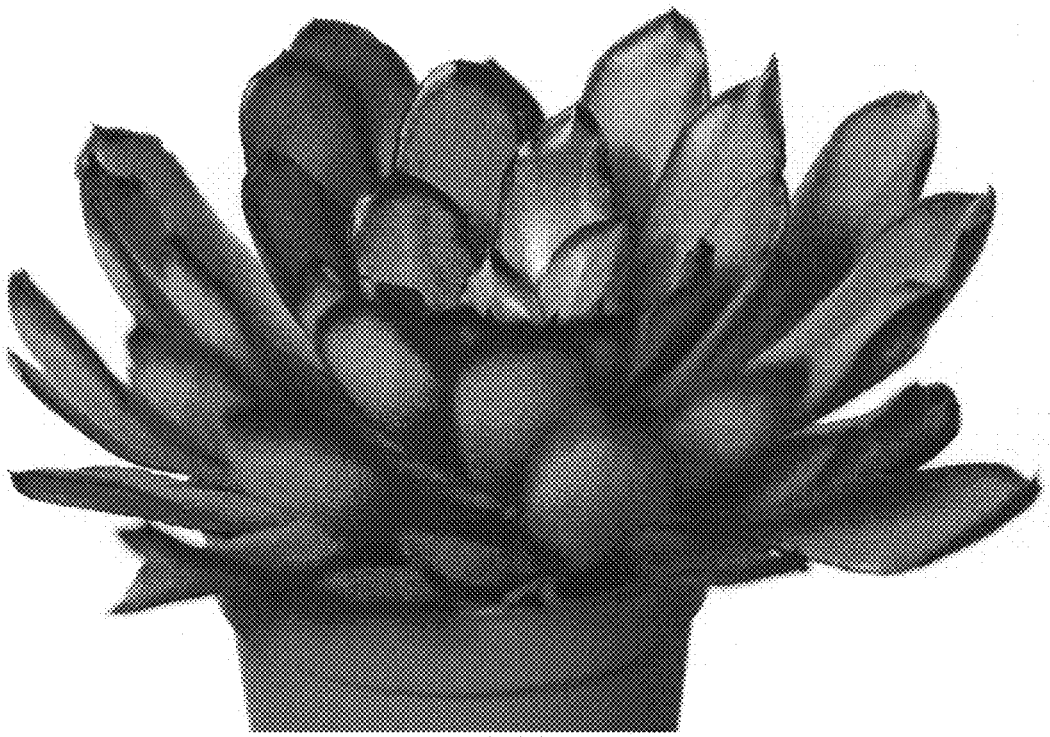
FIG. 1 illustrates, as nearly true as it is reasonably possible to make the same in color photographs of this type, an exemplary plant of 'OVPEARLSO8' grown in a commercial greenhouse in Bleiswijk, the Netherlands. This plant is approximately 1 year old, shown planted in a 12 cm container.
Figure 2:
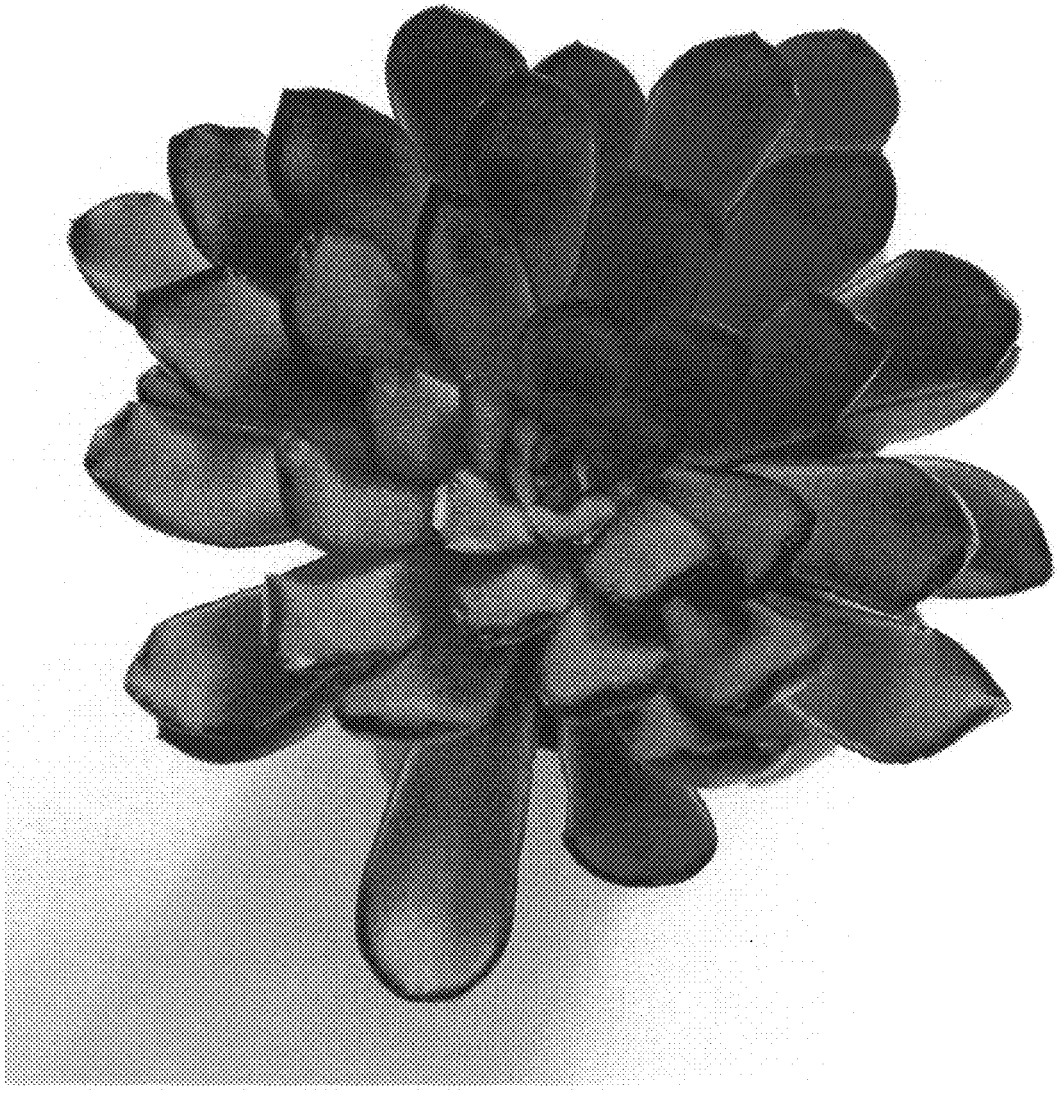
FIG. 2 illustrates, as nearly true as it is reasonably possible to make the same in color photographs of this type, the typical foliage arrangement of 'OVPEARLSO8'.
Figure 3:
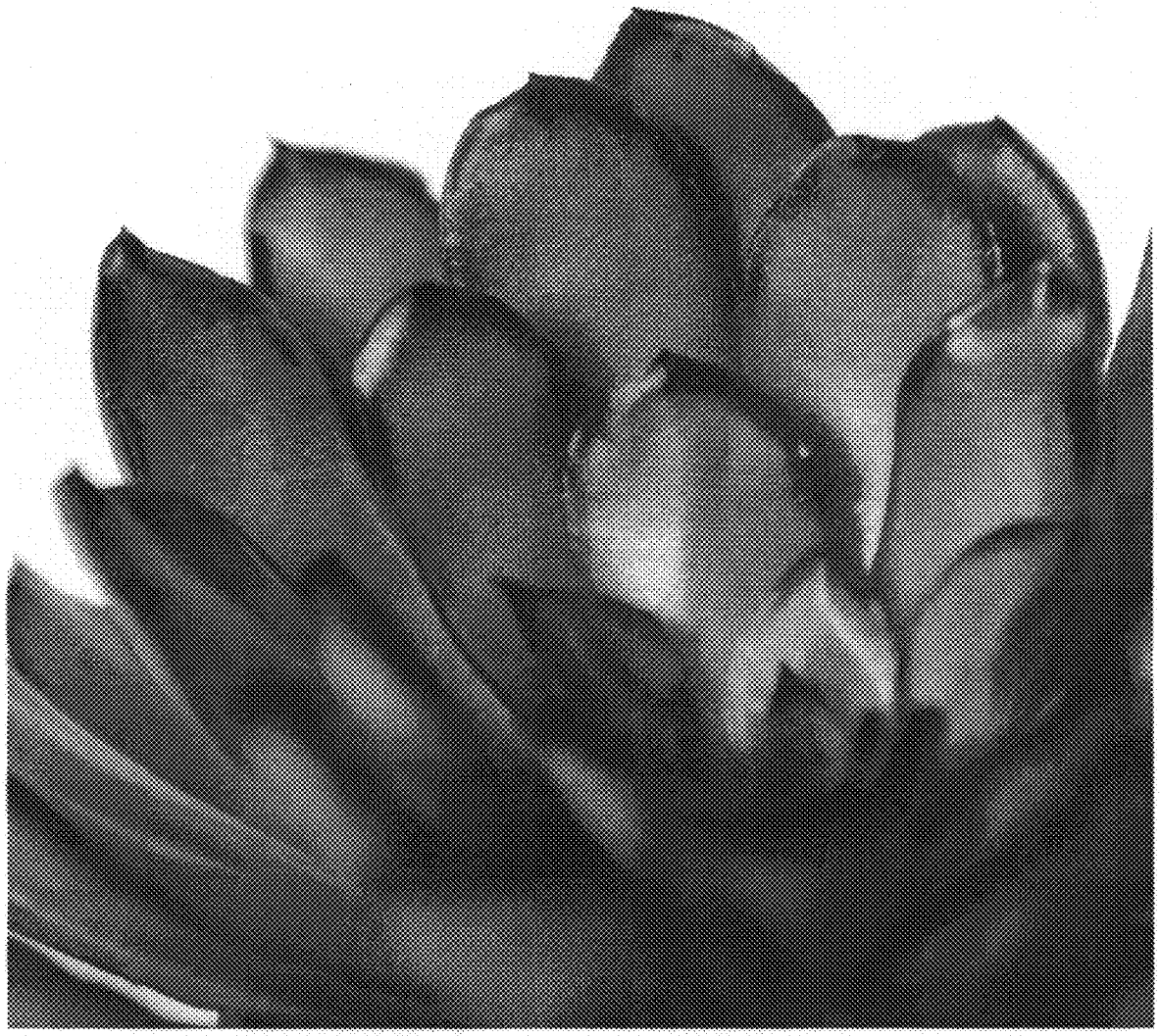
FIG. 3 illustrates, as nearly true as it is reasonably possible to make the same in color photographs of this type, the adaxial surface of the mature foliage 'OVPEARLSO8'.
Figure 4:
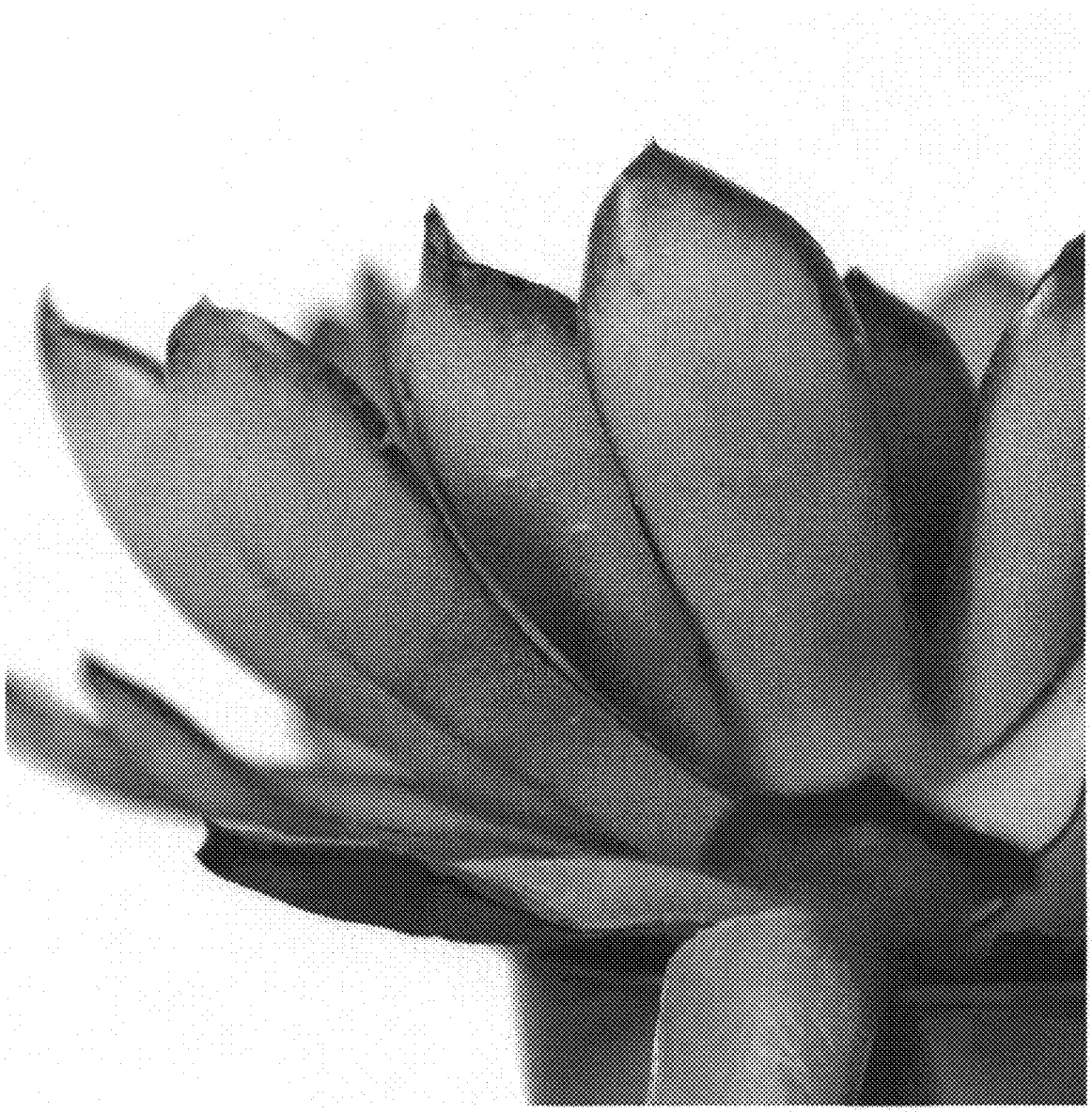
FIG. 4 illustrates, as nearly true as it is reasonably possible to make the same in color photographs of this type, the abaxial surface of the mature foliage 'OVPEARLSO8'.

The following observations and measurements made in November of 2019 describe averages from a sample set of six specimens of 1 year old 'OVPEARLSO8' plants grown in 5.5 cm nursery containers at commercial greenhouse in Bleiswijk, the Netherlands. Plants were produced using conventional greenhouse production protocols for *Echeveria* which consisted of minimal subsurface irrigation, fertilizer applications, and chemical pest control measures against thrips as required. No other chemical pest and disease control measures were taken. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'OVPEARLSO8' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2015 (sixth edition).

A botanical description of 'OVPEARLSO8' and a comparison with the parent and closest known comparator is provided below.

Plant description:

*Growth habit.*—Succulent perennial with foliage growing in a non-branched basal rosette.

*Plant form.*—Flattened.

*Height from soil level to top of foliar plane.*—4.6 cm.

*Plant spread.*—Average of 11.0 cm.

*Growth rate.*—Slow to moderately fast.

*Plant vigor.*—Moderately vigorous.

*Propagation.*—Type — Leaf cuttings. Time to initiate rooting — Approximately 5 weeks at an approximate temperature of 21 degrees Celsius. Crop time — Approximately 1 year to produce a marketable plant in a 12 cm container.

*Disease and pest resistance or susceptibility.*—Neither resistance nor susceptibility to typical *Echeveria* pests and diseases has been observed.

*Environmental tolerances.*—Adapt to, at least, USDA Zones 10 to 12 and temperatures as high as 40 degrees Celsius; moderate tolerance to rain yet drought tolerant once established; high tolerance to wind.

Root system:

*General.*—Fine, well-branched fibrous roots.

Stems:

*Branching habit.*—No stems or branches; leaves arranged in a basal rosette.

Foliage:

*Arrangement.*—Rosette.

*Division.*—Simple.

*Attachment.*—Sessile.

*Quantity.*—Approximately 54 leaves per rosette.

*Shape.*—Oblanceolate to narrow obovate.

*Dimensions.*—5.1 cm long, 1.5 cm wide, and 0.5 cm thick, on average.

*Aspect.*—Very slightly concave; distal portion of the leaf is curled upward at an approximate angle of 25 degrees to the proximal portion of the leaf. Margins at and near the apex are involute.

*Attitude.*—Foliage is held upright and outward at and near the center of the rosette and becomes progressively more relaxed towards the outer whorls of foliage.

*Apex.*—Bluntly apiculate.

*Base.*—Long cuneate.

*Margin.*—Entire; not undulated.

*Pubescence, texture and luster of the adaxial surface.*—Glabrous, smooth, and moderately glossy.

*Pubescence, texture and luster of the abaxial surface.*—Glabrous, smooth, and moderately glossy.

*Color.*—Juvenile foliage, adaxial surface — Greyed-green, nearest to RHS 191A; margined greyed-purple, nearest to a mixture of RHS 187B and 187C, and becoming darker at the apex, nearest to in between RHS N186C and 187A. Juvenile foliage, abaxial surface — Greyed-green, nearest to RHS 191A; margined greyed-purple, nearest to a mixture of RHS 187B and 187C, and becoming darker at the apex, nearest to in between RHS N186C and 187A. Mature foliage, adaxial surface — Yellow-green, nearest to RHS 147B, and fading lighter towards the base, nearest to RHS 147C; base is strongly suffused with purple, nearest to RHS 75B; margined greyed-purple, nearest to RHS 187D, and becoming darker at the apex, nearest to RHS N186C. Mature foliage, abaxial surface — Nearest to in between yellow-green and greyed-green, RHS N148B and 194A; fading to yellow-green towards the base, nearest to RHS N148D; base is strongly suffused with purple, nearest to a mixture of RHS 75A and 75B; central zone of the leaf is lightly suffused with greyed-purple, nearest to RHS 185C; suffused with greyed-purple towards the apex, nearest to RHS 187C; margined greyed-purple, nearest to a mixture of RHS 187C and 187D, and becoming darker at the apex, nearest to RHS N186C.

*Venation.*—Pattern — No venation is visible. Color, adaxial surface — No venation is visible. Color, abaxial surface — No venation is visible.

*Petiole.*—No petiole; leaves are sessile.

Inflorescence: No flowering has been observed to date.

Comparisons with the parent plant: Plants of the new cultivar 'OVPEARLSO8' differ from the parent, an unnamed *Echeveria pulidonis* plant (not patented) in the following characteristics described in Table 1 below.

TABLE 1

| Characteristic | 'OVPEARLS08' | The parent. |
|---|---|---|
| Foliage size. | Longer and narrower than the parent. | Shorter and broader than 'OVPEARLS08'. |
| Foliage glaucosity. | Foliage is not glaucescent. | Moderately glaucescent. |
| General coloration of the mature foliage. | Appearing as a darker shade of green by comparison to the parent. | Appearing as a lighter shade of green by comparison to 'OVPEARLS08'. |

TABLE 1-continued

| Characteristic | 'OVPEARLS08' | The parent. |
|---|---|---|
| General coloration of the leaf margins. | Conspicuously margined greyed-purple, generally appearing | Less conspicuously margined red. dark red. |

Comparisons with the closest known comparator: Plants of the new cultivar 'OVPEARLSO8' differ from *Echeveria* 'OVPEARLSO5' (U.S. patent application Ser. No. 16/899,822), which is the closest known comparator, in the following characteristics described in Table 2 below.

TABLE 2

| Characteristic | 'OVPEARLS08' | 'OVPEARLS05' |
|---|---|---|
| Plant profile and growth habit. | Flattened profile with foliage more loosely held in a basal rosette. | Globular profile with foliage more tightly held in a basal rosette. |
| Abundance of foliage | Less abundant than 'OVPEARLS05'. | More abundant than 'OVPEARLS08'. |

TABLE 2-continued

| Characteristic | 'OVPEARLS08' | 'OVPEARLS05' |
|---|---|---|
| Foliage aspect. | Distal portion of the leaf is curled upward; margins at and near the apex are involute. | Distal portion of the leaf is curled upward; margins are not involute. |
| Foliage glaucosity. | Not glaucescent. | Strongly glaucescent. |
| General coloration of the mature foliage. | Yellow-green to greyed-green, generally appearing as a medium yellow-green coloration. | Greyed-green. |
| General coloration of the foliar margins. | Narrowly margined with a darker shade of greyed-purple; becoming more broadly margined at the apex. | Distally margined with a lighter shade of greyed-purple. |
| Color suffusion of the abaxial surface of the mature foliage. | Lightly suffused with greyed-purple across most of the leaf surface. | Heavily suffused with greyed-purple towards and at the apex. |

That which is claimed is:

1. A new and distinct variety of *Echeveria* plant named 'OVPEARLSO8', substantially as described and illustrated herein.

* * * * *